United States Patent [19]

Tsau et al.

[11] 4,439,460

[45] Mar. 27, 1984

[54] DIPEPTIDE SWEETENER SULFATE AND SULFONATE SALTS

[75] Inventors: Josef H. Tsau, Prospect Heights; James G. Young, Northbrook, both of Ill.

[73] Assignee: G. D. Searle & Co., Skokie, Ill.

[21] Appl. No.: 383,393

[22] Filed: Jun. 1, 1982

[51] Int. Cl.$^3$ .............................................. A23L 1/236
[52] U.S. Cl. ............................... 426/548; 260/112.5 R
[58] Field of Search ................... 426/548; 260/112.5 R

[56] References Cited

U.S. PATENT DOCUMENTS

| | | | |
|---|---|---|---|
| 3,907,766 | 9/1975 | Fujino et al. ................ | 260/112.5 R |
| 3,959,245 | 5/1976 | Nakajima et al. ............ | 260/112.5 R |
| 4,029,701 | 6/1977 | Haas et al. .................... | 426/548 |
| 4,031,258 | 6/1977 | Haas et al. .................... | 426/548 |
| 4,153,737 | 5/1979 | Berg et al. .................... | 426/548 |

*Primary Examiner*—Joseph M. Golian
*Attorney, Agent, or Firm*—Steven M. Odre; John J. McDonnell

[57] ABSTRACT

Aspartyl dipeptide sweetener sulfate and alkyl sulfonate salts are described which have high thermal stability and a fast rate of dissolution in aqueous media. These salts can be almost universally substituted in place of sugar and are effective in baking and cold drink applications.

9 Claims, No Drawings

DIPEPTIDE SWEETENER SULFATE AND SULFONATE SALTS

BACKGROUND OF THE INVENTION

The present invention relates to low calorie dipeptide sweetener salts which can be used in heated or cooked foods and have no disagreeable aftertaste. More specifically, the invention relates to aspartyl dipeptide sweetener sulfate and organosulfonate salts which have a high thermal stability and dissolve rapidly in aqueous media.

Known dipeptide sweeteners are aspartyl-substituted alanine compounds having many times the sweetening power of sucrose. They were discovered in the 1960's and have been developed as low calorie substitutes for sugar. They do not have the bitter aftertaste of artificial sweeteners and since they are composed of natural amino acids, they are naturally assimilated.

Pharmacologically acceptable acid salts of the dipeptide sweeteners have been described as having about the same sweetening effect as the free base sweeteners. In addition, they dissolve quickly in aqueous media; see U.S. Pat. Nos. 4,029,701 and 3,714,139. Known dipeptide salts include the hydrohalide salts, the hydrogen sulfate salt, the dihydrogen phosphate salt, and similar salts as described in U.S. Pat. Nos. 4,031,258 and 4,029,701.

Despite the attractiveness of the use of the dipeptide sweeteners and their acid salts as sweeteners, difficulties remain. The free base and known salt forms of the sweetners, in general, exhibit little thermal stability. Consequently, when used in foodstuffs which require cooking or when mixed with food ingredients and put through a heating process such as pasteurization, they tend to be thermally degraded. Moreover, their low thermal stability adversely affects their shelf lives. As a result, the free base and known salt forms of sweeteners are not particularly useful for multipurpose foodstuff applications and cannot be universally substituted in place of sugar.

SUMMARY OF THE INVENTION

It is, therefore, an object of the invention to develop a dipeptide sweetener salt which is useful in almost all sweetening applications. Another object is the production of a single sweetener salt which can be almost universally substituted for sugar. Further objects include development of a sweetener salt having high thermal stability, a long shelf life and a high rate of aqueous dissolution. A specific object of the invention is the development of an aspartyl dipeptide sweetener salt having these properties.

In accordance with these objects, it has been discovered that dipeptide sweetener sulfate and organosulfonate salts have substantially high thermal stability and, in addition, exhibit a substantially high rate of dissolution in aqueous media. The dipeptide sweetener sulfate and organosulfonate salts respectively have the formulas:

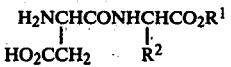

[APS.H]$_2$SO$_4$ and [APS.H]SO$_3$R

I  II wherein APS is an aspartyl dipeptide sweetener and R is alkyl of one to three carbons. These salts show high thermal stability in such applications as baked goods, puddings, candy, gelatin and hot beverages, quickly dissolve in food to be sweetened and have a long shelf life.

Some embodiments of the aspartyl dipeptide sweetener group (APS) include those of the formula:

H$_2$NCHCONHCHCO$_2$R$^1$　　　III
　|　　　　　|
HO$_2$CCH$_2$　　R$^2$ wherein R$^1$ is alkyl of one to six carbons and R$^2$ is phenyl, phenylalkylenyl or cyclohexylalkylenyl, with the alkylenyl group having from 1 to 5 carbons. Preferred forms of the APS group include those of formula III wherein R$^1$ is methyl and R$^2$ is benzyl.

A further preferred sweetener salt is one of the formula:

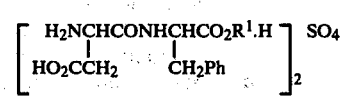

$$\left[ \begin{array}{c} \text{H}_2\text{NCHCONHCHCO}_2\text{R}^1.\text{H} \\ | \qquad\qquad | \\ \text{HO}_2\text{CCH}_2 \qquad \text{CH}_2\text{Ph} \end{array} \right]_2 \text{SO}_4 \qquad \text{IV}$$

An especially preferred sweetener salt is one of formula IV wherein R$^1$ is methyl.

The invention is further directed to foods and pharmaceutical formulations sweetened with a sweetener salt of formula I or II. The food comprises a mixture, slurry, dough, emulsion or paste of dry, fatty, oily or moist foodstuff ingredients in combination with the sweetener salt. Preferred forms of foodstuff ingredients comprise a baking dough, a dressing emulsion and a candy slurry. In addition, the food comprises a substantially dry soft drink foodstuff mixture in combination with the sweetener salt. A preferred form of the drink mixture comprises a compacted tablet.

The pharmaceutical formulations include tablets, liquids, elixers, syrups and similar formulated medicines which are to be sweetened. The sweetener wil mask the unpleasant taste typical of such medicines as penicillin, tetracycline and the like.

There is also provided according to the invention a novel process for preparation of the dipeptide sweetener salts. This process comprises preparing the sulfate or organosulfonate salt by dispersing the free base dipeptide sweetener in a minimum amount of a warm, polar medium such as water which contains the salt forming acid and then adding a warm, less polar, miscible solvent to precipitate the salt. In addition, this process can be used to prepare almost all dipeptide sweetener acid and base salts such as the hydrochloride salt and the sodium bisulfate salt. This process will yield high amounts of the salts in very pure states relative to the yields and purities provided by other methods.

DETAILED DESCRIPTION OF THE INVENTION

Dipeptide sweetener sulfate and organosulfonate salts of formulas I and II show substantial thermal stability and dissolve quickly in aqueous media. In addition, the factors generating enhanced thermal stability also lengthen the effective shelf life of the salts.

The low thermal stability shown by known acid dipeptide sweetener salts such as the hydrochloride and the bisulfate correlates with the low thermal stability of the free base forms of the dipeptide sweeteners. It follows that acid dipeptide sweetener salts generally would not be expected to have substantially high thermal stability.

It is surprising, therefore, that the dipeptide sweetener sulfate and sulfonate salts of the invention, which are acid salts, exhibit thermal stabilities which permit their effective use at minimum sweetening level amounts and under cooking, heating or baking conditions. Furthermore, it is surprising to find that the salts of the invention exhibit a very fast rate of dissolution in cold, aqueous media. Consequently, the salts of the invention can be almost universally substituted in place of sugar. They can be used in both hot and cold food and beverage applications whereas the free base and known salt forms of dipeptide sweeteners can not.

To prepare the salts of the invention, a dipeptide sweetener is mixed with a minimum amount of a highly polar solvent containing the appropriate acid for salt formation so that the weight ratio of sweetener to polar solvent is from about 30 percent to 50 percent. The amount of acid, i.e. sulfuric acid or sulfonic acid ($RSO_3H$), typically employed will be about an equivalent, i.e., one-half and one molar amounts respectively. During this step, the mixture may remain at ambient temperature or may be gently warmed to a temperature of about 40° to 60°, preferably 50°. If the mixture is warmed, salt formation will tend to proceed from a homogeneous solution, (while at lower temperatures, the mixture may remain cloudy and heterogeneous.) In general, there is a dynamic equilibrium between solid and dissolved forms of the sweetener which will cause formation of the salt even though the mixture is heterogeneous. Typically, with warming, a clear solution will be obtained.

After stirring and optionally warming the aqueous mixture for approximately 2 to 60 minutes, preferably 5 to 10 minutes a moderately polar organic solvent, which is miscible with the highly polar solvent and which has been warmed to an equivalent temperature, is added to the mixture. The amount of moderately polar solvent to be used should approximately be five to fifteen times the amount of highly polar solvent present, preferrably about ten times the amount. The conversion of the medium from a highly polar to a moderately polar system causes dissolution of any free base sweetener and impurities such as dipeptide acid and diketopiperazines which may be present and precipitation of the salt. Cooling can also be employed to precipitate additional salt from the medium.

Useful highly polar solvents include, but are not limited to, water, dimethyl sulfoxide, dialkyl formamide having one to two carbons in each alkyl group, and alkyl alcohols of one to four carbon atoms. The moderately polar solvent used must be chosen so that its polarity is less then that of the particular highly polar solvent used. Useful moderately polar solvents include, but are not limited to, alkyl alcohols of one to four carbon atoms, dialkyl ketones of three to six carbon atoms, aliphatic esters of three to six carbon atoms, chlorinated hydrocarbons of one to three carbons, hydrocarbons of five to eight carbons and other similar organic liquids. Preferred highly polar solvents are water and alkyl alcohol. Preferred moderately polar solvents are alkyl alcohol and chlorinated hydrocarbons. Especially preferred highly polar and moderately polar solvents respectively are water and alcohol.

If there is a significant amount of undissolved solid present during the process, then the change in physical appearance of the undissolved solids indicates salt formation. In a water or water-organic solvent medium, the salt appears as a fiberous, thick, cloud-like precipitate which tends to coagulate and form a gelled mixture. This can be contrasted with free base dipeptide sweetener which appears as a finely divided, particulate, low viscosity suspension.

It is significant to note that the conditions of heat, water and acid, in general, will cause hydrolysis and degradation of dipeptides. It follows that treatment of a dipeptide sweetener in the foregoing manner would usually be avoided since the sweetener would be expected to be destroyed. Nevertheless, this does not happen. It is believed that under the conditions of the process, the rate of salt formation and precipitation effectively prevent hydrolysis.

Other processes which are useful for preparing the salts of the invention include spray drying, freeze drying, lyophilization or drum drying. While these methods and the foregoing method will produce a dipeptide sweetener salt having high thermal stability, the method conceived according to the invention provides a salt having a moderately higher rate of dissolution and a very high purity. The reasons for the improved rate of dissolution as a function of the process are not understood.

Thermal decomposition and shelf life stability tests conducted upon samples of some salts of the invention, the free base dipeptide sweetener, the hydrochloride salt and the hydrogen sulfate salt illustrate the enhanced thermal stability of the salts of the invention. In the thermal decomposition tests, analytical examination of the residue present after seven minutes, fifteen minutes, or twenty-five minutes heating at about 170° C. shows that the sulfate salt of the invention exhibits substantial thermal stability while the comparative reference examples show significant degradation. The free base dipeptide sweetener and its bisulfate salt will show as much as 85 percent degradation and the hydrochloride salt will show at least about 45 percent degradation while the sulfate and methyl sulfonate salts of the invention will exhibit less than about 10 percent and about 30 percent degradation respectively under these conditions. In the shelf life stability tests, the sulfate salt of the invention typically shows less degradation than the hydrochloride salt after heating under accelerated conditions such as about 85° for about 15 days or 70° for about 15 days in an atmosphere having 100 percent humidity.

The thermal stability of the salts of the invention is further demonstrated by cake baking tests. In this test sweetened yellow cakes are prepared following well-known procedures and using the appropriate ingredients but substituting dipeptide sweetener for sugar. Use of examples of salts of the invention and reference dipeptides and salts such as the hydrochloride will produce eight-inch yellow cakes which are ready for sweetener content comparison. The cakes are typically baked at 350° Fahrenheit (about 175° C.) for about thirty to forty-five minutes. Taking core sections of the sample cakes and analyzing for dipeptide sweetener content allows determination of the percent degradation of the form of the dipeptide sweetener used. In a typical thermal stability cake test, a cake baked with the sulfate salt of the invention will have about 50 percent more dipeptide sweetener in it than a cake baked with the hydrochloride salt; compare, for example, about 34 percent sweetener recovery for the sulfate with about 25 percent for the hydrochloride.

A taste test of the baked dipeptide sweetened yellow cakes can also be conducted under standard single blind conditions. Panel taste testing will show that the dipeptide sweetener sulfate salt of the invention can produce a cake sweetness approximately equal to that of sugar while the free base dipeptide sweetener will typically produce cakes with little sweetness and a flat taste.

Rate of dissolution studies of the sulfate and sulfonate salts of the invention in comparison to known salts such as the hydrochloride and bisulfate salts illustrate that the salts of the invention generally exhibit high dissolution rates similar to that of the hydrochloride. Moreover, the sulfate salt surprisingly has a dissolution rate which is at least approximately five to six times faster than the rate of the corresponding hydrochloride salt. In a typical sulfate rate example, a sweetening amount of the sulfate salt will completely dissolve in refrigerated lemonade without stirring. The corresponding hydrochloride will require significant time and stirring to dissolve in refrigerated lemonade.

During thermal decomposition of dipeptide sweeteners, the degradation products produced include the individual amino acid composing the dipeptide, and diketopiperazines formed by amino acid cyclization. These products do not exhibit the sweet taste of the dipeptide sweetener. Therefore, since thermal degradation destroys the primary attribute of the sweetener, large amounts of sweetener would be needed to sweeten effectively baked foods, candy and liquids. Plainly, this is undesirable because there would also be large amounts of degradation products present.

The dipeptide sweetener salts of the invention solve this problem and fulfill a need to have a single effective dipeptide sweetener for general use in both cold and hot food applications. The salts rapidly dissolve in cold aqueous media. Hence, they are effective sweeteners for soft drink applications and cold beverages. Moreover, the salts have enhanced thermal stability. Hence, they are effective sweeteners for baking and food cooking applications and have a long shelf life.

In typical applications, the dipeptide sweetener salts of the invention can be used alone or as a formulation to sweeten dry and liquid foodstuffs. Formulations of the salt may include inert food bulking agents such as gums, dextrins, maltose, hydrolyzed starches and the like. These formulations can be used to produce sweeteners having the same spoon for spoon sweetness levels as sugar. Typical applications for formulated sweetener would include sweetening cereal and fruit. Prepackaged cake mixes and other dry foodstuff mixes can also be formulated using the dipeptide sweetener salts in amounts equivalent to the sweetness level for sugar and taking into account the minor amount of degradation occurring during baking.

The processes to prepare such foodstuffs are simple. Physically mixing the sweetener salt with the foodstuff to be prepared will typically be sufficient to allow uniform and thorough sweetening. The levels of sweetener to be used will be those which approximate sugar sweetness levels. While these levels can in general be determined empirically by tasting comparative samples, it will typically be sufficient to use the molar amount of salt equivalent to about 19 mg of methyl aspartyl-phenylalanine as the equivalent of about 5 grams of sugar.

It is believed that thorough distribution of the sweetener salt in foodstuff mixture to be baked or cooked is facilitated by the high dissolution rate. The salt diffuses throughout the water phase of the dough, pudding or mix because it is readily soluble therein. The sweetener, in turn, is distributed throughout the mix as it is carried by the water phase. Consequently, it is thought that a fast rate of dissolution and high thermal stability are both beneficial for baking purposes.

A further advantage is the higher apparent sweetness of the fast dissolving salts. When tasted, the ease with which they dissolve quickly loads the sense of taste. This, in turn, creates the sensation of a very sweet taste compared to the taste of slower dissolving salts.

Aqueous solutions and beverages containing the sweetener salts of the invention can also be simply prepared. Mixing, shaking, agitating alone or in combination with heat and stirring steps will allow preparation of such sweetened liquids. Ice cold solutions and mixtures of aqueous liquids, beverages, and the sweetener salts can also be prepared by mixing of the sweetener and the other ingredients in aqueous or other solutions. A preferred formulation for a beverage premix is a compressed tablet containing the salt and the other solid ingredients. It will be advantageous for prolonged storage of beverage foodstuffs incorporating the sweetener salts to employ substantially dry mixes which can be reconstituted with water, carbonated water and the like, at the time of preparation. The salts will undergo some degradation upon prolonged contact with water.

A liquid sweetening concentrate, which can be used immediately to sweeten foodstuffs and beverages or as a processing aid in the preparation of sweetened foods, can be prepared from the sweetener salts of the invention by saturating a water solution with the sweetener salt. Typically, such water solutions will contain about ten to sixty percent by weight sweetener salt. They can be prepared by simple methods such as agitation, admixture, stirring, or other similar combination of the aqueous solution and the sweetener salt. Auxiliary heating may be employed if necessary.

Concentrated sweetener solutions can be used in place of the dry sweetener form to sweeten beverages and dry food stuffs such as cereals, coffee, tea, lemonade, water, and other flavored liquid solutions or suspensions. The concentrate serves as a processing aid which enables quick and substantially complete distribution of the sweetener. In a typical example, the sweetener solution is placed in a dispensing apparatus from which the sweetener can be accurately metered. The solution is then sprayed, dripped or otherwise measured into the foodstuff during its preparation.

Typical foodstuff and beverage applications for the sweetener salts of the invention include those materials which can be packaged as foods or beverage mixtures containing little water. These include cake and cookie mixes, pudding mixes, soft drink mixes, candy mixes, gelatin mixes, and other similar food mixes which contain dry ingredients or in addition contain organic fats and oils. Examples incorporating fats and oils would include salad dressing, mayonnaise, mustard, prepared food systems containing organic oils and fats, and oil emulsions in minor amounts of water.

The following examples further illustrate details for the preparation and testing of the salts of the invention. The invention, which is fully set forth in the foregoing disclosure, is not to be construed as being limited either in spirit or scope by these examples. Those skilled in the art will readily understand that known variations and the conditions and processes of the following preparative procedures and testing regiment can also be used to prepare the salts of the invention and food stuffs and beverages incorporating them. All temperatures are in degrees celsius unless otherwise noted.

EXAMPLE 1

Bis(hydrogen aspartylphenylalanine methyl ester) sulfate

Sulfuric acid (96%, 1.66 g) was dissolved in distilled water (40 ml) and heated to about 40°. To this solution was added aspartylphenylalanine methyl ester (10.0 g) and the mixture was stirred. After the ester had dissolved to produce a clear solution, ethanol (400 ml), warmed to about 60°, was added with stirring. The solution was quickly filtered and the filtrate cooled to about 5° to precipitate the sulfate salt. The precipitated salt was filtered, washed with cold ethanol and dried in a vacuum at about 50° for about 2 hours to yield about 11 g of the above-titled salt. The physical characterizing data for this sulfate salt are given in Table 1.

Examples of the sulfonate salts of the invention were prepared using the foregoing procedure and substituting the appropriate organic sulfonic acid ($RSO_3H$) for sulfuric acid. The physical characterizing data for the sulfonate salts prepared are summarized in Table 1.

The sulfonate salts have the formula:

[aspartyl phenylalanine-H]$SO_3R$

TABLE 1

Sulfonate Salts

HPLC Assay*

| Example | R | Sulfur Content (%) Theory | Sulfur Content (%) Found | APM Content (%) Theory | APM Content (%) Found | DKP (%) | AP (%) | Water (%) |
|---|---|---|---|---|---|---|---|---|
| 1 | N/A* | 4.66 | 4.78 | 85.7 | 83.4 | Nd* | 0.14 | 0.56 |
| 2 | methyl | 8.20 | 7.83 | 75.4 | 73.2 | 0.1 | 0.5 | 3.5 |

*The high performance liquid chromatography (HPLC) analysis was conducted using standard techniques and an analytical HPLC system manufactured Water Associates, Milford, Mass. The column was a Dupont Zorbax C-8 (trademark of E. I. Dupont, Inc., Wilmington, Delaware) column measuring 15 cm by 4.6 mm. The mobile phase was a mixture of acetonitrile, tetrahydrofuran, and 0.05M aqueous sodium phosphate at a ratio of 4:1:45. UV detection of product was measured at 210 nm. The flow rate was 2 ml per min and the injection volume was 10 microl. Typical retention times are aspartylphenylalanine methyl ester (APM) 4.3 min; diketopiperazine (DKP) 2.2 min; aspartylphenylalanine (AP) 1.5 min. DKP and AP are degradation products typically found as impurities in APM. N/A is not applicable. Nd is not detected. The water percentage was determined by the Karl Fischer titration method.

EXAMPLE 3

Thermal Stability Examination

Samples of the salts of Examples 1 and 2 having weights equivalent to about 40 mg of APM and reference samples (40 mg) of free base aspartylphenylalanine methyl ester (APM) and the corresponding hydrochloride dihydrogen phosphate ($H_2PO_4$) and bisulfate ($HSO_4$) salts having weights equivalent to about 40 mg APM were placed in individual 10 ml beakers and put in an oven pre-heated to 170° C. The samples were allowed to bake for predetermined times (7, 15 and 25 minutes) after which they were removed from the oven and analyzed by HPLC using the foregoing HPLC methods. The results of the tests on the salts of the invention and the reference compounds are summarized in Table 2.

TABLE 2

| Sample | Thermal Stability % Degradation 7 Minutes (170° C.) | 15 Minutes (170° C.) | 25 Minutes (170° C.) | Physical Appearance after 25 Minutes at 170° C. |
|---|---|---|---|---|
| Ex. 1 (sulfate) | 1.3 | 0 | 5.5 | white cryst. powder |
| Ex. 2 (methyl sulfonate) | 0.0 | 0.5 | 28.0 | off white powder |
| A | 0 | 22.2 | 87.6 | light-gray material |
| B | 2 | 8.5 | 44.7 | melted, light-brown mass |
| C | 62.8 | 78.2 | 89.2 | melted colorless mass |
| D | 0.1 | 60.6 | 86.6 | yellow powder |

A is aspartylphenylalanine methyl ester (APM)
B is aspartylphenylalanine methyl ester hydrochloride
C is aspartylphenylalanine methyl ester bisulfate
D is aspartylphenylalanine phosphate, monobasic

EXAMPLE 4

Thermal Stability Studies in Baked Cake

Yellow cakes were baked following a standard recipe, but substituting a dipeptide sweetener or its salt and Maltrin M-100 (a modified maltodextrin starch bulking agent) for sugar. The liquid ingredients were creamed together then folded into a sifted mixture of the dry ingredients. The resulting dough was placed in a greased 8-inch cake pan and baked at 350° for 40 minutes. Three cakes were baked in this manner; cake 1 contained (APM-H)$_2$SO$_4$, cake 2 contained APM-HCl, cake 3 contained APM.

The liquid ingredients included milk (193 g), shortening (54 g), egg (53 g, 1 egg), vanilla (3.6 g); the dry ingredients included flour (167 g), baking powder (6.9 g), salt (3.4 g), maltrin M-100 (126.5 g) dipeptide sweetener salt: (APM-H)$_2$SO$_4$ (cake 1) (1.2 g), APM-HCl (cake 2) (1.2 g), APM (cake 3) (1.0 g).

Core samples were taken from each of the three cakes and the samples were analyzed by HPLC methods as described in Example 1. The HPLC analytical results are summarized in Table 3.

TABLE 3

| | Cake Analysis | | | |
|---|---|---|---|---|
| | APM %* | DKP %* | AP %* | taste |
| Cake 1 | 33.8 | 41 | 1.7 | sweet |
| Cake 2 | 25.5 | 35.5 | 1.8 | sweet |
| Cake 3 | 11 | — | — | slightly sweet |

Cake 1 - (APM—H)$_2$SO$_4$
Cake 2 - APM—HCl
Cake 3 - APM
APM is aspartylphenylalanine methyl ester.
*DKP is diketopiperazine, a degradation product of APM.
*AP is aspartyl phenylalanine, a degradation product of APM.

EXAMPLE 5

Rate of Dissolution Studies

Samples of the salts of Examples 1, 2 and the APM hydrochloride and corresponding bisulfate and dihydrogen phosphate salts were employed to determine relative dissolution rates in beverage media. The amount of salt used in each instance was calculated to be equimolar with 57 mg of APM. The tests were conducted in four types of liquid beverage media; (1) refrigerated carbonated water (240 ml), (2) refrigerated lemonade without sugar (240 ml), (3) refrigerated coffee (80 ml), (4) coffee at ambient temperature (80 ml). The dissolution rates in medium 1 were measured without stirring and the rates in 2, 3 and 4 were measured with stirring. Dissolution was deemed complete when solid particles or a cloudy appearing medium were no longer present. The results are summarized in Table 4.

as described above in order to determine percent decomposition. The results are summarized in Table 5.

TABLE 5

Shelf Life Determination
HPLC Assay Results (% composition)

| | 1.70° Initial* | | | 6.8 days* | | | 14.7 days* | | | (APM % Initial) |
|---|---|---|---|---|---|---|---|---|---|---|
| | APM | DKP | AP | APM | DKP | AP | APM | DKP | AP | |
| Ex.1 | 84.8 | nd | nd | 83.9 | nd | nd | 82.1 | nd | .20 | 96.7 |
| A | 96.6 | 1.0 | nd | 95.3 | 1.1 | nd | 92.6 | 1.2 | 0.21 | 95.9 |
| B | 80.2 | nd | nd | 77.7 | .25 | .33 | 75.1 | .60 | .36 | 93.6 |
| | 2.85° C. | | | | | | | | | |
| Ex 1 | Same as above | | | 83.0 | 0.15 | nd | 80.9 | .08 | .20 | 95.4 |
| A | Same as above | | | 95.2 | 1.6 | nd | 91.7 | 2.0 | .20 | 94.9 |
| B | Same as above | | | 62.1 | 4.0 | 1.1 | 46.0 | 3.2 | 1.6 | 57.3 |

Ex 1 is (APM.H)$_2$SO$_4$
A is APM
B is APM.HCl
DKP is diketopiperazine
AP is aspartylphenylalanine
nd is not detected.
*The numbers are percents of compound composition (APM, DKP and AP) present at the time of analysis. The last column shows the percent of APM remaining in the samples after 14.7 days relative to the initial APM present.

TABLE 4

| | Dissolution Rates | | | |
|---|---|---|---|---|
| | Media Dissolution Times (seconds) | | | |
| Sample | 1+ | 2+ | 3+ | 4+ |
| Ex. 1 | 22 | About 0 | 24 | 22 |
| Ex. 2 | 168 | 250 | — | 167 |
| B | 120 | 52 | 94 | 90 |
| C | — | — | — | 330 |
| D | — | — | — | 600 |

+1 is refrigerated carbonated water
+2 is refrigerated lemonade with no sugar
+3 is refrigerated coffee
+4 is ambient temperature coffee
Ex 1 is (APM.H)$_2$SO$_4$
Ex 2 is (APM.H)SO$_3$CH$_3$
B is APM hydrochloride
C is (APM.H)HSO$_4$
D is (APM.H)H$_2$PO$_4$

EXAMPLE 6

Shelf Life Determination

Two sets of samples of the APM sulfate salt of Example 1, APM hydrochloride and APM each having a weight equivalent to 40 ml APM were placed in ovens which contained an open beaker of water. The first set of samples was heated at 70° and 100 percent humidity for 14.7 days. The second set of samples was heated at 85° and atmospheric humidity for 14.7 days. The samples were periodically analyzed by the HPLC method

What is claimed is:
1. A dipeptide sweetener salt of the formula

[APM.H]$_2$SO$_4$ or [APM.H]SO$_3$R wherein APM represents aspartyl-phenylalanine methyl ester and R is lower alkyl containing 1 to 3 carbon atoms.
2. A sweetener solution comprising a sweetener salt according to claim 1 in an aqueous solution.
3. A solution according to claim 2 wherein the concentration of the salt is at least 8 percent by weight.
4. A sweetened food comprising a mixture of dry, fatty or oily foodstuff ingredients in combination with a sweetener salt of claim 1.
5. A food according to claim 4 wherein the salt is

[aspartyl-phenylalanine methyl ester.H]$_2$SO$_4$.

6. A food according to claim 4 wherein the foodstuff comprises wheat, rice or oat flour based ingredients useful for preparation of leavened or unleavened baked goods which are processed by heating.
7. A food according to claim 4 wherein the foodstuff comprises animal or vegetable oil based ingredients useful for preparation of dressings or sauces.
8. A food according to claim 4 wherein the foodstuff comprises modified, starch based ingredients useful for preparation of candies.
9. A food according to claim 4 wherein the foodstuff comprises a dry soft drink mixture.

* * * * *